United States Patent [19]

Sawanishi et al.

[11] 4,055,493

[45] Oct. 25, 1977

[54] METHOD FOR OPENING A HIGH-DENSITY PACKED COLUMN IN LIQUID CHROMATOGRAPHY

[75] Inventors: Shigeru Sawanishi; Masahiko Ozaki; Kikuji Katagawa, all of Okayama, Japan

[73] Assignee: Japan Exlan Company Limited, Osaka, Japan

[21] Appl. No.: 745,920

[22] Filed: Nov. 29, 1976

[30] Foreign Application Priority Data

Dec. 1, 1975 Japan .................................. 50-143679

[51] Int. Cl.$^2$ ........................................... B01D 15/08
[52] U.S. Cl. ...................................... 210/31 C; 55/67; 210/71
[58] Field of Search ................. 210/31 C, 32, 274, 71; 55/67, 386, 62

[56] References Cited

U.S. PATENT DOCUMENTS

| | | | |
|---|---|---|---|
| 3,032,953 | 5/1962 | Micheletti | 55/62 |
| 3,873,514 | 3/1975 | Chu et al. | 210/31 C |
| 3,926,800 | 12/1975 | Stephens | 210/31 C |

*Primary Examiner*—John Adee
*Attorney, Agent, or Firm*—Wenderoth, Lind & Ponack

[57] ABSTRACT

Method for opening a high-density packed column in liquid chromatography wherein a large number of components in a solution are separated by means of a column in which a swollen gel is packed at a high density. The improvement involves passing air through the column while heating the column to a temperature above at least 40° C. to shrink the volume of the packed column, and then opening the column. According to this process, there is no loss in the expensive gel nor contamination thereof and yet it's operating efficiency is greatly improved.

10 Claims, No Drawings

METHOD FOR OPENING A HIGH-DENSITY PACKED COLUMN IN LIQUID CHROMATOGRAPHY

The present invention relates to a method for opening a high-density packed column in liquid chromatography. More specifically, the invention relates to a method for opening a high-density packed column in liquid chromatography, particularly in its industrial apparatus, for separating a large number of components in a solution by means of a column packed with a swollen gel at a high density, whereby upon opening said high-density packed column there is no loss in expensive gel or no contamination of the gel, and yet its operating efficiency can be remarkably improved.

So far, liquid chromatography has been applied to a variety of areas as one of the means for separating mixed components, and as an analytical means high-speed liquid chromatography has achieved rapid progress in recent years. Such separating techniques do not remain only as laboratory analytical means but also they are very useful in large-scale fractioning and industrial separation, so that they are utilized in various fields of industry such as pharmacy, foodstuff, petrochemical and synthetic chemical products, natural organic chemical compounds, etc.

In such fields where liquid chromatography is utilized industrially, a column having a large diameter is used as the gel packing column from the viewpoint of economy. In such cases, various problems incidental to scale enlargement which are difficult to anticipate from experiments using small-diameter columns, for example lowering of separating power, are liable to occur. Thus, in industrial liquid chromatography wherein large-diameter columns are used, it has been found quite effective to use columns packed at a high density with a gel such as shown in J. Chromatog. 47 (1970) pp 490–493, in order to prevent such lowering in separating power.

To increase packing density of gel in a column, a method wherein a volume-variable column as described in Disclosed (Kokai) Japanese Patent Application No. 91964/1974, a method of packing using a pressure packing apparatus, or a dry-packing method wherein dry gel is packed and then swollen to obtain a high density is employed. Thus, a longterm, continuous separating operation is repeated using the thus-obtained high density packed column. During the longterm operation by such a liquid chromatographic apparatus, there occur troubles such as soiling and clogging of filters fixed at the upper and lower caps of the column, or damage of the filters, or leakage of the gel from the column; and also there will be need to replace the gel or to change the packing density. In such cases, it becomes necessary to open the column packed with swollen gel at a high density.

In such cases, if the column caps are opened without any treatment of the gel, the gel in the column will increase in volume, so that a part of the gel may overflow out of the column, which results in a loss of the expensive gel or in further contamination of the gel. Also, after opening the column, when one desires to pack the gel again into the column at a high density, it becomes necessary to use the above-mentioned special packing apparatus or to remove a large amount of the swollen gel from the column and then dry it by means of a special drying apparatus. Also, there is a method wherein, in order to prevent overflowing of the swollen gel, the swelling agent absorbed by the gel is replaced with a poor solvent. By this method, however, not only a large amount of an expensive chemical is consumed, but also the effluent at that time must be carefully treated so that it does not cause any environmental pollution.

Thus, the operation of opening the high density packed column to remove the gel from the column, the operation of packing gel into the column, the operation of replacing filter nets equipped in the column, etc. are indispensable for long-term working of industrial apparatus for liquid chromatography. But the conventional methods are extremely inconvenient and require much labor and a special apparatus or expensive chemicals, also requiring a long time for these operations. Therefore, when industrial separating operation is carried out by liquid chromatography, the standstill time of the apparatus becomes long, and the productive efficiency is greatly lowered, thus inflicting a heavy loss, so that improvement of the operation has been desired.

In the light of such a situation, we made an intensive study to solve this problem. As a result, we have found that, prior to opening the column packed at a high density with a swollen gel, when dry air is passed through the column while heating the column, the swollen gel in the column, without being removed from the column, can be dried gradually, whereby the volume of the gel can be effectively reduced. The present invention has been accomplished on the basis of this discovery.

Thus, the present invention is characterized in that, in liquid chromatography for separating a number of components in a solution by means of a column packed with a swollen gel at a high density, the column is opened after the volume of the packed gel has been reduced by passing dry air through the column while heating the column to a temperature above at least 40° C.

According to the present invention, it is possible to allow a swollen gel packed at a high density to reduce its volume efficiently and effectively within the column, without exerting any adverse influence on its separating power, so that the column caps can be opened without any loss of the gel or without causing any gel contamination. Accordingly, it is possible to perform removal of the gel and exchange of the filters within a very short time, and besides the labor of the operation can be reduced. As a matter of course, it greatly heightens the industrial importance of the present invention that the invention makes unnecessary the drying of the swollen gel by means of a special drier, the use of a large amount of expensive chemicals or the use of complicated operations or installations. The phenomenon in which the gel packed in the column in a swollen state, especially in a water-swollen state can be effectively reduced in volume by passing dry air, is supposed to result from the fact that the gel has a small moisture absorption power because of its weak binding power with water, though the gel itself is hydrophilic. By knowing the cause and effect of this phenomenon, it has become possible for the first time to reduce the volume of swollen gel in the column.

The swollen gels packed in the column in the present invention are those generally called hydrophilic gels such as well-known dextran gel, dextran gel derivatives, polyacrylamide gel, polyethylene glycol dimethacrylate gel, etc. and they are sold on the market under the name of Sephadex G 10 to 200, Sephadex LH-20 (Pharmacial Fine Chemicals), Bio-Gel P 2 to 300 (Bio-Rad Laboratories), Merckogel PGM 2000 (E. Merck) or Chromagel P (Dojin Yakkagaku).

As the liquid chromatographic apparatus to which the method of the present invention can be applied, any apparatus can be used which are so designed as to be able to separate a large number of components in the solution by means of the column packed with the gel. Especially, the method of the present invention can display its effect to the maximum when applied to large-scale industrial apparatus. As regards the size of the columns used in such liquid chromatographic apparatus, the method of the present invention is effectively applicable to medium scale columns having a diameter of the order of 10 cm. to 20 cm. or even to huge ones having a diameter of 37 cm., 1 m. or 1.8 m.

The column, packed at a high density with a swollen gel, to which the present invention is applicable is generally maintained at a vacant space ratio (ratio of the vacant space among the swollen gel granules to the inner volume of the column) of less than 40%, preferably 20 - 35%, and the gel within the column becomes swollen with a solvent used for the actual separating operation, generally with water.

To display the effect of the present invention sufficiently for a high-density packed column in the practice of the method of the invention, it is necessary to heat the column to a temperature above at least 40° C., preferably from 60° to 100° C., and where the column is not subjected to such a heating operation it becomes difficult to attain the object of the invention. The upper limit of the heating temperature of the column is up to the denaturation or degradation temperature of the packed gel, and it is different depending on the kind of the packed gel, though a heating temperature above 120° C. should be generally avoided. The heating operation may be performed by heating the column exteriorly of its outer wall by means of a heating jacket or the like, using a heat medium such as hot water, hot air or steam, or by heating the dry air which is passed through the column, by a suitable heating means.

The dry air which is passed through the column is such that its relative humidity at the temperature within the column is less than 100%, and air having a relative humidity generally below 80%, preferably below 50%, is advantageously used for the present invention. It is desirable from the standpoint of apparatus design that such dry air is directly introduced into the column from the treating liquid inlet or outlet through the treating liquid conduit connected to the air conduit, but it is possible to introduce dry air into the column from an air supply opening equipped for that purpose to the apparatus.

The passing direction of air is not restricted so far as dry air is passed through the column, but it is particularly effective for the present invention to pass dry air from the top of the column toward bottom. Dry air is passed through the column by introducing it under pressure into the column from the air supply opening or by suction from the air discharge opening. Also, to facilitate the removal of wet air from the column, a method is preferably employed wherein the air discharge opening is brought to reduced pressure. The flow rate of the air through the column is varied depending on the kind, particle diameter and packing density of the gel and on the ventilation time elapsed, but values within the range of 0.005 - 1.5 l/cm$^2$.min, preferably 0.01 - 1.0 /cm$^2$.min (liters per unit sectional area per minute) are employed.

It is possible to dry the swollen gel within the column completely by passing a sufficient amount of dry air through the column according to the present invention, but it is the usual practice to pass dry air through the column for a time sufficient for volume shrinkage of the degree that the gel in the column does not overflow upon opening the high-density packed column. The time required for shrinking the volume of the gel in the column to a necessary minimum depends on the humidity and flow rate of dry air, column size, heating conditions, etc. Anyway, after shrinking the volume of the gel in the column by passing dry air for a time sufficient to attain the object of the invention, the column caps are opened.

Thus, when the column is opened after the gel in the column is sufficiently shrinked in volume according to the present invention, there is no inconvenience of overflowing swollen gel to lose the expensive gel so that the gel is not newly contaminated, and also the column opening operation becomes very simple. In addition, the operation of removal, exchange and re-packing of gel, alternation of packing density and replacement of filter nets can be performed smoothly in a short time. These are marked features of the present invention. Furthermore, when the gel shrinked in volume according to the method of the present invention is packed into the column again and is returned to the prescribed swollen state with a solvent, the column can be restored to its initial characteristics.

For a better understanding of the present invention, examples are set forth hereunder, but the scope of the invention is not limited by these particular examples.

EXAMPLE 1

A column for industrial use, one meter in height and 40 cm. in diameter, was prepared by packing it with Sephadex G-10 (Pharmacia Fine Chemicals), a cross-linked gel of dextran, at a packing density higher than the density which the gel would take when subjected to free swelling in water at atmospheric pressure.

From the liquid flow outlet at the top of the column packed at that high density with the swollen gel, compressed air was introduced under a gauge pressure of 1 kg/cm$^2$ so as to pass through the column, and then the air was discharged from the liquid flow inlet at the bottom. The column was heated from outside by circulating hot water of 80° C. through the column jacket. It resulted that about 24 hours were required to shrink the volume of the gel within the column to the extent that there was no difficulty in opening the column, namely to the extent that the gel did not overflow from the column upon opening it.

It was confirmed that the column swollen with water again after the volume shrinkage was not different from before the above-mentioned operation in various performances such as column parameter, theoretical number of steps, separating power, etc.

EXAMPLE 2

In the same manner as in Example 1 except for using Bio-Gel P-2 (Bio-Rad Laboratories), a cross-linked gel of polyacrylamide, compressed air was passed through the column packed with the swollen gel at a high density. After about 30 hours, the ventilation was stopped and the column was opened. The packed gel exhibited a smaller volume than the column volume and did not overflow from the column.

What we claim is:

1. A method for opening a high-density packed column in liquid chromatography wherein a large number of components in a solution are separated by means of a column in which a swollen gel is packed at a high density, characterized by passing air through the column while heating the column to a temperature above at least 40° C. to shrink the volume of the packed column, and then opening the column.

2. A method as claimed in claim 1 wherein the density of the swollen gel in the column is maintained at a vacant space ratio of less than 40%.

3. A method as claimed in claim 1 wherein the density of the swollen gel in the column is maintained at a vacant space ratio of 20 – 35%.

4. A method as claimed in claim 1 wherein the column heating temperature is 60°– 100° C.

5. A method as claimed in claim 1 wherein the dry air to be passed through the column is that having a relative humidity of less than 100%.

6. A method as claimed in claim 1 wherein the dry air to be passed through the column is that having a relative humidity below 80%.

7. A method as claimed in claim 1 wherein the dry air to be passed through the column is that having a relative humidity below 50%.

8. A method as claimed in claim 1 wherein the dry air is passed from the top of the column toward bottom.

9. A method as claimed in claim 1 wherein the flow rate of the dry air is 0.005 – 1.5 $l/cm^2$.min. per unit cross-sectional area of the column.

10. A method as claimed in claim 1 wherein the flow rate of the dry air is 0.01 – 1.0 $l/cm^2$.min. per unit cross-sectional area of the column.

* * * * *